(12) United States Patent
Song et al.

(10) Patent No.: US 10,959,863 B2
(45) Date of Patent: Mar. 30, 2021

(54) MULTI-DIMENSIONAL SURFACE ELECTROMYOGRAM SIGNAL PROSTHETIC HAND CONTROL METHOD BASED ON PRINCIPAL COMPONENT ANALYSIS

(71) Applicant: SOUTHEAST UNIVERSITY, Jiangsu (CN)

(72) Inventors: Aiguo Song, Jiangsu (CN); Xuhui Hu, Jiangsu (CN); Hong Zeng, Jiangsu (CN); Baoguo Xu, Jiangsu (CN); Huijun Li, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 151 days.

(21) Appl. No.: 16/475,680

(22) PCT Filed: May 23, 2018

(86) PCT No.: PCT/CN2018/088055
§ 371 (c)(1),
(2) Date: Jul. 3, 2019

(87) PCT Pub. No.: WO2018/233435
PCT Pub. Date: Dec. 27, 2018

(65) Prior Publication Data
US 2019/0343662 A1 Nov. 14, 2019

(30) Foreign Application Priority Data
Jun. 20, 2017 (CN) .......................... 201710477543.6

(51) Int. Cl.
*A61F 2/72* (2006.01)
*G16H 50/20* (2018.01)
(Continued)

(52) U.S. Cl.
CPC ................ *A61F 2/72* (2013.01); *A61F 2/586* (2013.01); *G06F 3/017* (2013.01); *G16H 50/20* (2018.01);
(Continued)

(58) Field of Classification Search
CPC ..... A61F 2/72; A61F 2002/704; B25J 9/1612; B25J 9/00; G06F 3/017
See application file for complete search history.

(56) References Cited

U.S. PATENT DOCUMENTS 7,333,090 B2 * 2/2008 Tanaka ................... B25J 9/1656
345/158
10,285,616 B2 * 5/2019 Yoshioka ................ G06F 3/017
(Continued)

FOREIGN PATENT DOCUMENTS

CN 202235787 5/2012
CN 104586608 5/2015
(Continued)

OTHER PUBLICATIONS

"International Search Report (Form PCT/ISA/210) of PCT/CN2018/088055," dated Jul. 27, 2018, pp. 1-4.

*Primary Examiner* — Bruce E Snow
(74) *Attorney, Agent, or Firm* — JCIPRNET

(57) ABSTRACT

The present invention discloses a multi-dimensional surface electromyogram signal prosthetic hand control method based on principal component analysis. The method comprises the following steps. Wear an armlet provided with a 24-channel array electromyography sensor to a front arm of a subject, and respectively wear five finger joint attitude sensors at a distal phalanx of a thumb and at middle phalanxes of remaining fingers of the subject. Perform independent bending and stretching training on the five fingers of the subject, and meanwhile, collect data of an array electromyography sensor and data of the finger joint attitude sensors. Decouple the data of the array electromyography sensor by principal component analysis to form a finger motion training set. Perform data fitting on the finger motion training set by a neural network method, and con-
(Continued)

struct a finger continuous motion prediction model. Predict a current bending angle of the finger through the finger continuous motion model.

5 Claims, 3 Drawing Sheets

(51) Int. Cl.
    *A61F 2/58*     (2006.01)
    *G06F 3/01*     (2006.01)
    *A61F 2/70*     (2006.01)

(52) U.S. Cl.
    CPC ... *A61F 2002/587* (2013.01); *A61F 2002/701* (2013.01); *A61F 2002/704* (2013.01)

(56) References Cited

U.S. PATENT DOCUMENTS

| | | | |
|---|---|---|---|
| 10,543,111 B2 * | 1/2020 | Engeberg | A61F 2/72 |
| 10,852,835 B2 * | 12/2020 | Yetkin | G06F 3/014 |
| 2001/0014441 A1 * | 8/2001 | Hill | G06F 3/015 |
| | | | 434/236 |
| 2009/0327171 A1 * | 12/2009 | Tan | G06N 20/00 |
| | | | 706/12 |
| 2015/0346833 A1 * | 12/2015 | Jiang | G06F 3/017 |
| | | | 345/158 |
| 2016/0166409 A1 * | 6/2016 | Goldfarb | A61F 2/68 |
| | | | 623/25 |
| 2016/0313798 A1 * | 10/2016 | Connor | A61B 5/0488 |
| 2018/0178008 A1 * | 6/2018 | Bouton | A61B 5/16 |
| 2018/0221177 A1 * | 8/2018 | Kaltenbach | G06F 3/0346 |
| 2019/0212817 A1 * | 7/2019 | Kaifosh | G06F 3/017 |
| 2020/0265948 A1 * | 8/2020 | Lock | G06F 3/016 |
| 2020/0272240 A1 * | 8/2020 | Baranski | A61B 5/0488 |
| 2020/0326778 A1 * | 10/2020 | Asada | B25J 9/1694 |

FOREIGN PATENT DOCUMENTS

| | | |
|---|---|---|
| CN | 104665962 | 6/2015 |
| CN | 105943206 | 9/2016 |
| CN | 106236336 | 12/2016 |
| CN | 107378944 | 11/2017 |
| EP | 1043003 | 10/2000 |

* cited by examiner

MULTI-DIMENSIONAL SURFACE ELECTROMYOGRAM SIGNAL PROSTHETIC HAND CONTROL METHOD BASED ON PRINCIPAL COMPONENT ANALYSIS

CROSS-REFERENCE TO RELATED APPLICATION

This application is a 371 of international application of PCT application serial no. PCT/CN2018/088055, filed on May 23, 2018, which claims priority to and the benefit of China Patent Application No. 201710477543.6, filed on Jun. 20, 2017. The entirety of each of the above-mentioned patent applications is hereby incorporated by reference herein and made a part of this specification.

TECHNICAL FIELD

The present invention relates to a manipulator control method, and more particularly, to a multi-dimensional surface electromyogram signal prosthetic hand control method based on principal component analysis.

BACKGROUND

A bio-mechatronic dexterously manipulated prosthesis is an intelligent interaction device that can cooperate with environment, human and other robots, and can recognize a motion intention of an operator through collecting bioelectric signals of a human body. The study on artificial prosthesis can promote technological innovation in the field of rehabilitation engineering for functional reconstruction of the disabled, and extend and develop the scientific connotation of equipment manufacturing. The scientific and technological achievements can be radiately applied to high-end medical equipment, bio-mechatronic intelligent robots, hazardous environment exploration and disaster rescue equipment, national defense equipment, and other major fields related to the national economy and people's livelihood, with important strategic significance.

The surface electromyogram signal is a bio-electric signal that has captured wide attention at present. The surface electromyogram signal is favored by many researchers since it contains abundant information and is noninvasively collected. To recognize patterns of a discrete gesture motion is the most mature method to apply the surface electromyography to the interaction field. Compared with the classification of discrete motions, a continuous motion estimation of a joint is more valuable to realize smooth control over robot motions, but there are relatively fewer published research results in this field.

Since different subjects have different forearm muscle development degrees and different operating habits, it is often difficult to extract universal movement rules for all individuals.

The finger motions of human are very complicated, and the existing research mainly focuses on recognizing isolated gestures and rarely recognize continuous gestures. Principal component analysis is used in the technology to decouple the complicated muscle activity of the hand, and can analyze the continuous activity of each finger. At present, there is no literature to study the continuous motion estimation of the finger.

SUMMARY

Object of the invention: in order to overcome the defects in the prior art, the present invention provides a multi-dimensional surface electromyogram signal prosthetic hand control method which uses electromyography signals to recognize a motion intention of a human body and decouples electromyography data based on principal component analysis, so as to effectively predict and estimate a continuous motion of a finger.

Technical solution: the present invention provides a multi-dimensional surface electromyogram signal prosthetic hand control method based on principal component analysis, comprises the following steps.

(1) Wear an armlet provided with an array electromyography sensor to a front arm of a subject, and respectively wear five finger joint attitude sensors at a distal phalanx of a thumb and at middle phalanxes of remaining fingers of the subject, wherein the array electromyography sensor is a 24-channel array electromyography sensor.

(2) Perform independent bending and stretching training on the five fingers of the subject, and meanwhile, collect data of an array electromyography sensor and data of the finger joint attitude sensors.

(3) Decouple electromyography sensing data by principal component analysis to form a finger motion training set of the subject, wherein the finger motion training set is represented by a matrix, a number of rows of the matrix is a number of samples, a number of columns of the matrix is a number of channels of the array electromyography sensor, and original 24-dimensional data is reduced to 5-dimensional data by principal component analysis; and removing the sensor worn on the finger after the training is finished.

(4) Perform data fitting on the finger motion training set by a neural network method, and construct a finger continuous motion prediction model.

(5) Predicting a current bending angle of the finger through the finger continuous motion model in step (4).

The independent bending and stretching training on the five fingers in the step (2) specifically comprises: repeatedly bending and stretching each finger for ten times, pausing for 30 seconds after completing one round of motions of the five fingers, then performing a second set of motions, two sets of motions being performed in total; collecting and preprocessing electromyography signals in the training process, and stopping collecting during the pauses; and representing original electromyography data by a muscle activity; and the preprocessing comprising representation and normalization processing on the muscle activity of the electromyography signals, and quaternion solution of attitude data.

In the step (4), a three-layer neural network structure is used, five neurons are arranged in an input layer, 15 neurons are arranged in a hidden layer, and five neurons are arranged in an output layer; transmission functions of the hidden layer and the output layer of the neural network are a Sigmoid function and a linear function respectively; and the finger motion training set collected in the step (3) is used as a sample for error back propagation calculation to solve network parameters thereof.

In the step (5), after the current bending angle of the finger is predicted, a bending angle variation of the finger is converted into an actual control amount of a motor, which specifically comprises the following steps.

(6.1) Design an underactuated control model for a prosthetic hand finger.

(6.2) Calculate a motion equation of an estimated bending angle of the finger and a rotation angle of a stepping motor by analyzing a motion trajectory of the prosthetic hand finger.

(6.3) Substitute the estimated bending angle of the finger into the motion equation in the step (6.2) to obtain an output rotation angle of the stepping motor.

(6.4) Control the stepping motor to rotate at a corresponding angle through a microcontroller.

Beneficial effects: firstly, different from a traditional electromyography signal collection control system, the wearable electromyography armlet and the finger joint attitude sensors are used to respectively collect the surface electromyogram signals and the bending angle of the finger joint of the subject according to the present invention, a position of an electrode of the electromyography sensor is not strictly required, and a large amount of debugging time can be saved during training, so that individual neural network parameters can be trained for each training individual through the present invention, and a prediction precision is obviously improved within an allowable training time range; secondly, principal component analysis is used in the present invention to decouple a large amount of redundant data and pick up motion information related to the finger joint, which, on one hand, shortens a training time and an operation time of the neural network, and on the other hand, intuitively analyzes a connection between the electromyography signals and the continuous motions of the finger; and finally, the present invention applies an continuous motion estimation of the finger joint to bio-mechatronic dexterous hand control, and a proposed finger control strategy has the advantages of few control lines, stable operation, concise structure and the like.

DETAILED DESCRIPTION

Figure 1:
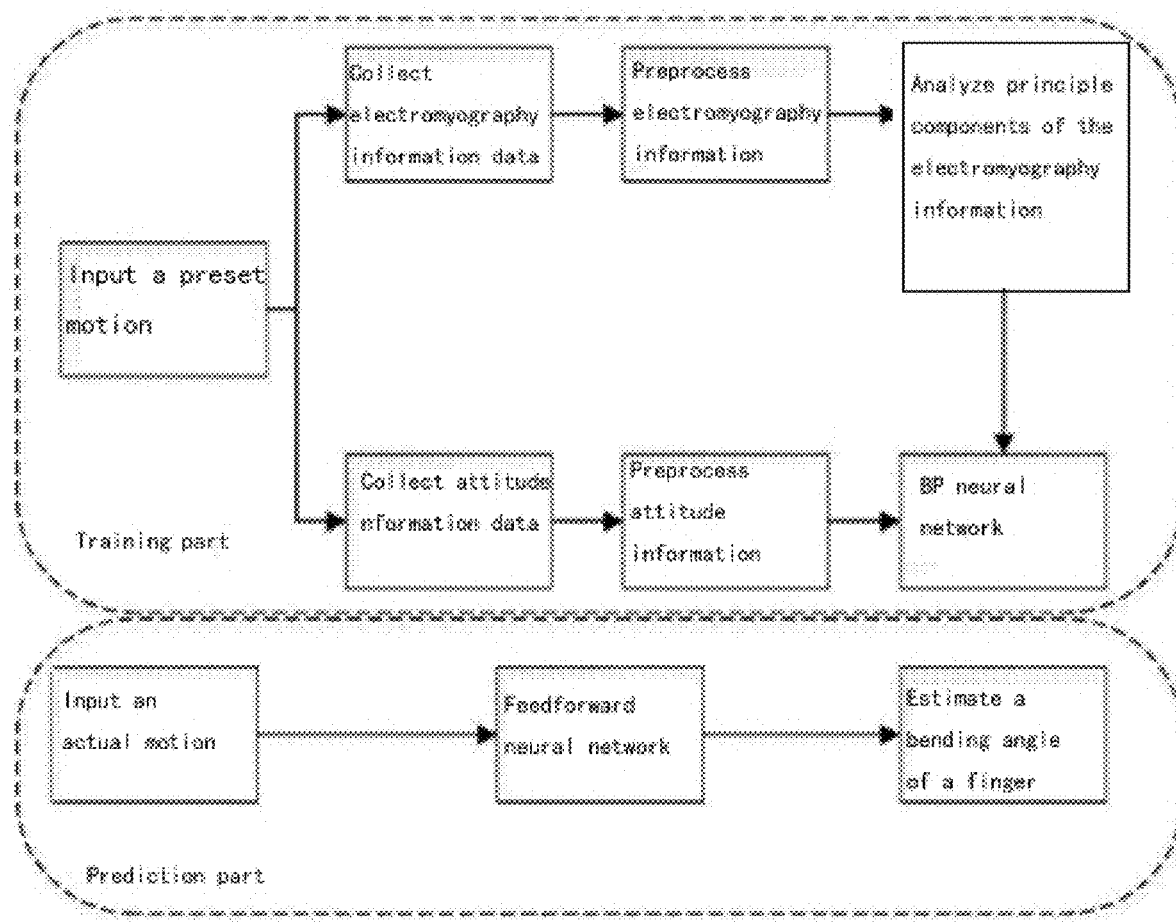
FIG. 1 is a flow chart of a method according to the present invention.

According to the present invention, multi-dimensional surface electromyography data is decoupled based on principal component analysis, and mainly comprises a training part and a prediction part according to an algorithm framework of supervised machine learning, as shown in FIG. 1.

The training part comprises the following.

a. Wear an array electromyography sensor and finger joint attitude sensors.

b. Train a subject according to preset prescribed motions, and meanwhile, collecting data of the array electromyography sensor and data of the finger joint attitude sensors by a computer.

c. Preprocess the data of the array electromyography sensor and the data of the finger joint attitude sensors, comprising signal processing procedures such as representation and normalization processing on the muscle activity of the electromyography signals, and quaternion solution of attitude data.

d. Package the data above in a matrix form and using the data as a training sample of a neural network, and calculate each connection weight of the neural network by Error Back Propagation (BP neural network). A feedforward neural network obtained is a finger continuous motion prediction model.

The prediction part comprises the following.

a. Wear the array electromyography sensor;

b. Perform operation on the feedforward neural network is performed every 10 ms, represent 24-dimensional electromyography data by a column vector, and then multiply the data by a transformation matrix of principal component analysis to obtain a 5-dimensional column vector; substitute the column vector into a trained neural network model for calculation, so as to obtain an estimated bending angle of a finger c. After the estimated bending angle of the finger is calculated by the neural network, convert a bending angle variation of the finger to an actual control amount of a motor.

The technical solution of the present invention is further described in detail hereinafter with reference to the embodiments and the drawings.

As a preferred solution, the embodiment specifically comprises the following steps.

(1) Wear a 24-channel array electromyography sensor and five finger joint attitude sensors correctly, wherein a wearing method for the sensors is given as follows.

(1.1) A subject is sitting with muscles in an upper arm relaxed; a forearm of the subject is horizontal and a wrist is relaxed, which is intended to reduce signal aliasing between electromyography signals generated by other additional motions of the upper arm and the wrist and electromyography signals generated by the motion of the hand as much as possible.

Figure 2A:
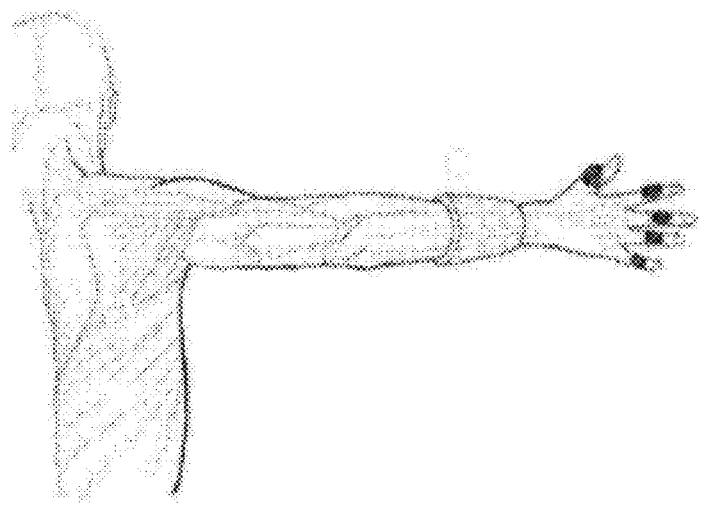
FIGS. 2(A) and 2(B) are wearing diagrams of an array electromyography sensor and finger joint attitude sensors.
Figure 2B:
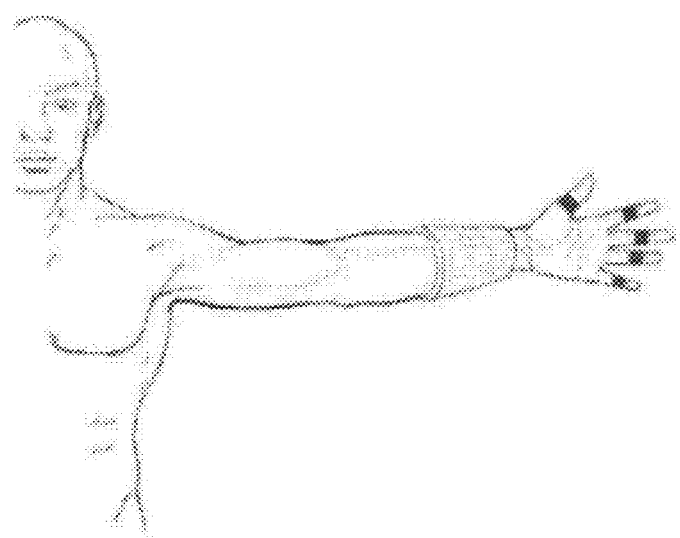

(1.2) Design an array electromyography sensor armlet regarding forearm sizes of different subjects, wherein the array electromyography sensor can be tightly attached to a skin surface to prevent an electrode on a surface of the sensor from shifting or separating from the skin by adjusting a tightness of the armlet, as shown in FIGS. 2(a) and 2(b).

(1.3) Wear the finger joint attitude sensors respectively at a distal phalange of a thumb and middle phalanges of remaining fingers, as shown in FIGS. 2(a) and 2(b).

(2) Train the subject according to the preset prescribed motions, and meanwhile, collect the data of the array electromyography sensor and the data of the finger joint attitude sensors by a computer, which specifically comprises the following steps.

Figure 3:
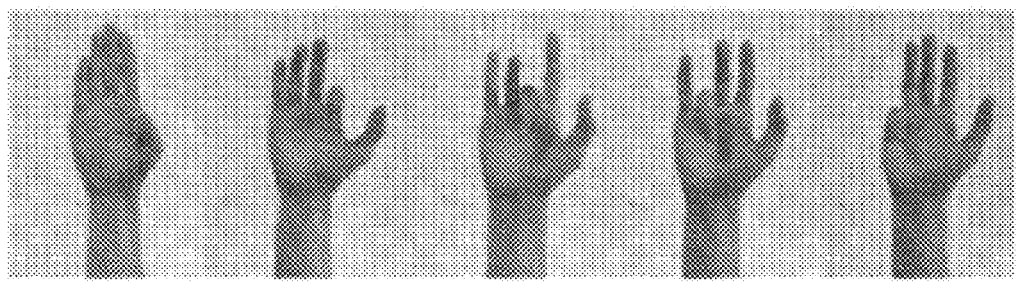
FIG. 3 is a preset motion set finished by a subject at a training stage specified in the present invention.

(2.1) Instruct the subject to perform independent bending and stretching training on the five fingers, repeat the bending and stretching each finger for ten times, pause for 30 seconds after completing the motions of the five fingers for one round, then perform a second set of motions, wherein two sets of motions are performed in total, as shown in FIG. 3.

(2.2) During a period from the beginning of the training to the end of the training, sample the electromyography signals at a sampling rate of 1 KHz, then respectively use Butterworth filters of 25 Hz and 4 Hz for high-pass and low-pass filtering, and finally obtain original preprocessed data of the electromyography signals at a collection frequency of 100 Hz by mean filtering.

(2.3) Reading data of a triaxial accelerometer and a gyroscope of the finger joint attitude sensor at a collection frequency of 100 Hz, and then obtain data of a triaxial attitude angle by a quaternion attitude solution algorithm; use one-dimensional data reflecting the bending angle of the finger as feedback data of the actual bending angle of the finger; and remove the sensor worn on the finger after training.

(3) Decouple the electromyography sensing data by principal component analysis to form a finger motion training set of the subject, wherein orthogonal transformation is used in the principal component analysis to change a linearly related vector set to a linearly independent vector set, the principal components are represented by vectors, and a number of the principal components is less than or equal to a number of column vectors in an original matrix, which specifically comprises the following steps.

(3.1) Normalize the electromyography data collected in the step (2.1), wherein the specific method comprises: calculating a mean value and a standard deviation of the same dimension data in the training sample firstly, and then subtracting the mean value from the original data in the same dimension and then dividing a value obtained by the standard deviation, and the formulas are as follows:

$$\overline{X}_j = \frac{\sum_{i=1}^{m} x_j^i}{m}, \quad \sigma = \sqrt{\frac{\sum_{i=1}^{m}(x_j^i - \overline{x_j})^2}{m}}, \text{ and } x_j^{norm(i)} = \frac{x_j - \overline{x_j}}{\sigma}.$$

(3.2) Calculate a covariance matrix is calculated according to the normalized data calculated in the step (3.1), and take the principal component column vectors in the first five columns as the transformation matrix of principal component analysis.

(3.3) Calculate the decoupled five-dimensional electromyography data by a matrix transformation formula.

(4) Performing data fitting on the finger motion training set by a neural network method, and construct a finger continuous motion prediction model, wherein: firstly, the data of the array electromyography sensor (after normalization) at any time and the data of the attitude sensors are formed into a pair of input and output training data, wherein the input data is used as a feature vector of the neural network and the output data is used as a label of the sample; then the input data is decoupled, and a 24-dimensional feature vector and the transformation matrix of principal component analysis are multiplied to obtain a decoupled 5-dimensional feature vector; and the use of a neural network classifier comprises two parts, i.e., a training process and a prediction process, wherein the decoupled samples obtained through calculation in the step (3.3) are firstly divided into a training set, a cross-validation set and a test set according to proportions of 60%, 20% and 20%; the sample data of the training set is used to calculate each connection weight of the neural network by Back Propagation (BP neural network); the cross-validation set is used to determine regularization parameters of the neural network and improve the prediction precision; and the test set is used as a quantitative index to measure the quality of the finger continuous motion prediction model.

(5) Predicting the current motion of the finger, i.e., the bending angles of the five fingers, by the finger continuous motion model in the step (4), wherein it can be seen from the specific embodiment that a frequency for collecting the data sample is 100 Hz; therefore, an executing period of the neural network is set as 10 ms in the present invention; assuming that the data obtained at a certain moment is the normalized 24-dimensional electromyography data, a preferred example of gesture intention recognition by the neural network classifier at that moment is given below.

(5.1) Represent the 24-dimensional electromyography data by a column vector, and then multiply the data by the transformation matrix of principal component analysis to obtain a 5-dimensional column vector. (5.2) Substitute the 5-dimensional column vectors in step (5.1) into the trained neural network model for calculation, and then obtain the expected finger bending angle.

(6) After the estimated bending angle of the finger is calculated by the neural network, convert the bending angle variation of the finger to the actual control amount of the motor, substituting the 5-dimensional column vector in the step (5.1) into the trained neural network model for calculation, so as to obtain the estimated bending angle of the finger.

The bending and stretching of the prosthetic hand finger specifically comprise the following steps.

Figure 4:
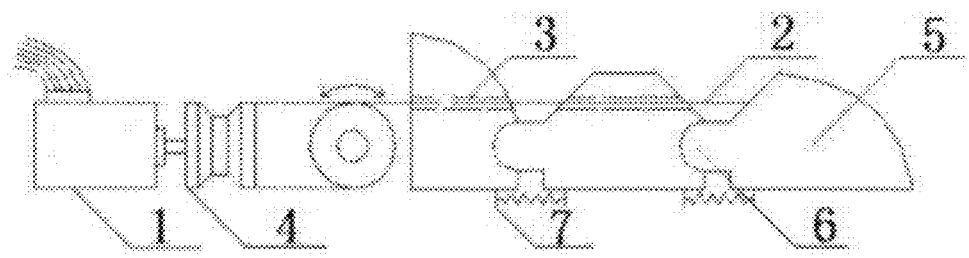
FIG. 4 is a diagram illustrating an underactuated control method for a prosthetic hand finger.

(1) Design an underactuated control model for the prosthetic hand finger as shown in FIG. 4, wherein a stainless steel wire 2 is wound on a reel 4 through a through hole 3, the inelastic stainless steel wire 2 is rotationally pulled by a stepping motor 1 to pull up a distal phalanx 5 of the prosthetic hand, and the distal phalanx 5 of the prosthetic hand rotates around a rotary joint 6 to simulate a bending motion of the finger; and a stretching motion of the hand finger can be simulated when the steel wire is loosened by a restoring force generated by a spring 7 between the phalanges.

(2) Calculate a motion equation of an estimated bending angle of the finger and a rotation angle of the stepping motor 1 through analyzing the motion trajectory of the prosthetic hand finger.

(3) Substitute the estimated bending angle of the finger into the motion equation above to obtain an output rotation angle of the stepping motor 1.

(4) Control the stepping motor 1 to rotate at a corresponding angle through a microcontroller (a single chip microcomputer and a computer).

The stepping motor 1 changes a rotation speed of a rotor thereof through applying a pulse of a certain frequency, and the rotation angle thereof is precisely positioned by a number of transmitted pulses. The current estimated bending angle of the finger is stored in a non-volatile storage unit in the system before the system is powered off, and when the system runs again, last running position of the motor can be confirmed, thus avoiding the stepping motor from performing zero adjustment for many times and preventing the stepping motor from running incorrectly.

As mentioned above, although the present invention has been described and illustrated with reference to specific preferred embodiments, the preferred embodiments shall not be construed as limiting the present invention. Various changes can be made in form and details without departing from the spirit and scope of the present invention as defined by the claims.

What is claimed is:

1. A multi-dimensional surface electromyogram signal prosthetic hand control method based on principal component analysis, comprising the following steps:

(1) wearing an armlet provided with an array electromyography sensor to a front arm of a subject, and respectively wearing five finger joint attitude sensors at a distal phalanx of a thumb and at middle phalanxes of remaining fingers of the subject, wherein the array electromyography sensor is a 24-channel array electromyography sensor;

(2) performing independent bending and stretching training on the five fingers of the subject, and meanwhile, collecting data of an array electromyography sensor and data of the finger joint attitude sensors;

(3) decoupling electromyography sensing data by a principal component analysis to form a finger motion training set of the subject, wherein the finger motion training set is represented by a matrix, a number of rows of the matrix is a number of samples, a number of columns of the matrix is a number of channels of the array electromyography sensor, and original 24-dimensional data is reduced to 5-dimensional data by principal component analysis; and removing the sensors worn on the fingers after the training is finished;

(4) performing data fitting on the finger motion training set by a neural network method, and constructing a finger continuous motion prediction model; and (5) predicting a current bending angle of the finger through the finger continuous motion model in the step (4).

2. The multi-dimensional surface electromyogram signal prosthetic hand control method according to claim 1, wherein the independent bending and stretching training on the five fingers in the step (2) specifically comprises: repeatedly bending and stretching each finger for ten times, pausing for 30 seconds after completing one round of motions of the five fingers, then performing a second set of motions, two sets of motions being performed in total; collecting and preprocessing the electromyography signals in the training process, and stopping collecting during the pauses; and representing original electromyography data by a muscle activity.

3. The multi-dimensional surface electromyogram signal prosthetic hand control method according to claim 2, wherein the preprocessing comprises representation and normalization processing on the muscle activity of the electromyography signals, and quaternion solution of attitude data.

4. The multi-dimensional surface electromyogram signal prosthetic hand control method according to claim 1, wherein in the step (4), a three-layer neural network structure is used, five neurons are arranged in an input layer, 15 neurons are arranged in a hidden layer, and five neurons are arranged in an output layer; transmission functions of the hidden layer and the output layer of the neural network are a Sigmoid function and a linear function respectively; and the finger motion training set collected in the step (3) is used as a sample for error back propagation calculation to solve network parameters thereof.

5. The multi-dimensional surface electromyogram signal prosthetic hand control method according to claim 1, wherein in the step (5), after the current bending angle of the finger is predicted, a bending angle variation of the finger is converted into an actual control amount of a motor, which specifically comprises the following steps of:

(6.1) designing an underactuated control model for a prosthetic hand finger;

(6.2) calculating a motion equation of an estimated bending angle of the finger and a rotation angle of a stepping motor by analyzing a motion trajectory of the prosthetic hand finger;

(6.3) substituting the estimated bending angle of the finger into the motion equation in the step (6.2) to obtain an output rotation angle of the stepping motor; and (6.4) controlling the stepping motor to rotate at a corresponding angle through a microcontroller.

* * * * *